(12) United States Patent
Su et al.

(10) Patent No.: US 10,980,573 B2
(45) Date of Patent: Apr. 20, 2021

(54) DEVICE FOR STABILIZATION OF BONE SEGMENT AND EXTENDING ASSEMBLY THEREOF

(71) Applicant: WILTROM CO., LTD., Zhubei (TW)

(72) Inventors: Yi-Chun Su, Zhubei (TW);
Chieh-Feng Lu, Zhubei (TW);
Yen-Ting Tseng, Zhubei (TW);
Huang-Chien Liang, Zhubei (TW)

(73) Assignee: Wiltrom Co., Ltd., Zhubei (TW)

( * ) Notice: Subject to any disclaimer, the term of this patent is extended or adjusted under 35 U.S.C. 154(b) by 118 days.

(21) Appl. No.: 16/123,607

(22) Filed: Sep. 6, 2018

(65) Prior Publication Data
US 2019/0069930 A1 Mar. 7, 2019

(30) Foreign Application Priority Data
Sep. 7, 2017 (TW) .................................. 106130690

(51) Int. Cl.
*A61B 17/70* (2006.01)
*A61B 17/56* (2006.01)
(Continued)

(52) U.S. Cl.
CPC ...... *A61B 17/7032* (2013.01); *A61B 17/7002* (2013.01); *A61B 17/7053* (2013.01); *A61B 17/7077* (2013.01); *A61B 17/7092* (2013.01); *A61B 17/00234* (2013.01); *A61B 2017/564* (2013.01); *A61B 2017/681* (2013.01); *A61F 2/442* (2013.01); *A61F 2/4611* (2013.01); *A61F 2002/4635* (2013.01)

(58) Field of Classification Search
CPC ............ A61B 17/7032; A61B 17/7034; A61B 17/7037; A61B 17/7083; A61B 17/7085; A61B 17/7086; A61B 17/7088; A61B 17/7079; A61B 17/708
See application file for complete search history.

(56) References Cited

U.S. PATENT DOCUMENTS 6,077,262 A * 6/2000 Schlapfer ........... A61B 17/7032
606/264
7,985,242 B2 * 7/2011 Forton ............... A61B 17/7086
606/246
(Continued)

FOREIGN PATENT DOCUMENTS

EP 2490608 A1 8/2012
WO WO-2012/058402 A2 5/2012

*Primary Examiner* — Ellen C Hammond
(74) *Attorney, Agent, or Firm* — Muncy, Geissler, Olds and Lowe, P.C.

(57) ABSTRACT

The present invention discloses a device for stabilization of bone segment and an extending assembly thereof. The device comprises a screw assembly, two supporting members and two extending members. The screw assembly comprises a receiver and an anchoring member. The receiver has a retainer and two opposite arms extending along the longitudinal axis of the device from the positions adjacent to the retainer. The anchoring member is connected to the retainer. The supporting members are connected to the arms respectively and extend along the longitudinal axis. Each one of the extending members has a through hole respectively. The extending members are connected to the arms with the supporting members passing through the through holes respectively.

18 Claims, 13 Drawing Sheets

(51) Int. Cl.
  *A61F 2/46* (2006.01)
  *A61B 17/00* (2006.01)
  *A61F 2/44* (2006.01)
  *A61B 17/68* (2006.01)

(56) References Cited

U.S. PATENT DOCUMENTS

| | | | | |
|---|---|---|---|---|
| 8,048,129 | B2* | 11/2011 | Forton | A61B 17/1655 606/252 |
| 9,918,751 | B2* | 3/2018 | Jackson | A61B 17/7008 |
| 10,166,049 | B2* | 1/2019 | Jackson | A61B 17/7008 |
| 2006/0111715 | A1 | 5/2006 | Jackson | |
| 2007/0073294 | A1* | 3/2007 | Chin | A61B 17/7091 606/86 A |
| 2008/0091213 | A1 | 4/2008 | Jackson | |
| 2012/0071886 | A1* | 3/2012 | Jackson | A61B 17/7008 606/104 |
| 2013/0096635 | A1* | 4/2013 | Wall | A61B 17/7079 606/305 |
| 2013/0304130 | A1* | 11/2013 | Jackson | A61B 17/7008 606/278 |
| 2015/0351810 | A1* | 12/2015 | Lindner | A61B 17/7032 606/278 |
| 2019/0059957 | A1* | 2/2019 | Heuer | A61B 17/7076 |

* cited by examiner

DEVICE FOR STABILIZATION OF BONE SEGMENT AND EXTENDING ASSEMBLY THEREOF

BACKGROUND OF THE INVENTION

1. Field of the Invention

The present invention relates generally to a device for stabilization of bone segment used in a surgery and an extending assembly thereof, and more particularly, to a device for stabilization of bone segment used in a minimally invasive surgery and an extending assembly thereof.

2. Description of the Related Art

The vertebral column is a major component of the central nervous system of the human body. Spinal disorders, especially in the lumbar region, often have a considerable impact on patients, causing pain, numbness, weakness, incontinence, dysuria, dyschezia, or other symptoms. The above symptoms are caused by a displacement of vertebrae putting pressure on the nerve or spinal cord. Due to different mechanisms, spinal disorders are clinically diagnosed as spinal disc herniation, spondylolisthesis, spinal stenosis or degenerative scoliosis. When symptoms are severe, the discomfort of patients usually cannot be relieved by correction, and spinal surgery is required to reposition the vertebrae. An important key to treatment success is the effective fixation of the repositioned vertebral body to prevent recurrent displacement.

The pedicle screw fixation system, a spinal implant device applied in vertebral fusion surgery, is the most stable and prevalent treatment for vertebral repositioning and fixation in traditional intervertebral disc resection, cervical degeneration and scoliosis correction. The pedicle screw fixation system includes a plurality of pedicle screws (also known as a screw assembly). In the case of a polyaxial pedicle screw, please refer to FIG. 1, each pedicle screw 9 generally includes a screw shaft 91, a receiver 92 (also known as a tulip) and a locking nut (also known as a nut). A common surgical procedure of the pedicle screw fixation system involves a first step of inserting pedicle screws 9 in pairs into the pedicles of each vertebra from both sides of the spinous processes of the vertebra. After that, rods are adjusted in advance in accordance with the normal vertebral curve, and then the locking screws are tightened into the receiver 92 by particular surgical instruments such as a pre-lock wrench and an anti-torque wrench in order to fix the rods within the receivers 92. Once the rods are fixed within the receivers, two adjacent vertebrae are correspondingly repositioned or stabilized.

Traditional spinal surgery is an open-type approach in which a midline incision is made on the back of the patient. The muscle tissue is cut open and then moved aside to expose the vertebrae, and the periosteum is peeled off from the vertebral section prior to the installation of the pedicle screw fixation system. The problems of this procedure are the large wound and the high blood loss; moreover, due to the invasive nature of the surgery, the recovery of the wound is a slow process. Furthermore, the reduced elasticity and fibrosis in the muscle tissue after surgery usually causes severe soreness, pain, and high risk of infection. These problems extend the length of the hospital stay and increase the overall medical expenses, which is a problem that has to be solved in terms of public health policy. Therefore, in recent years, minimally invasive surgery (MIS), which can significantly reduce the size of surgical wounds, has been gradually favored by surgeons and patients, and its clinical importance is also increasing.

Generally, a minimally invasive surgery is defined as one in which a surgical wound is less than 3 cm and anatomical damage is avoided as much as possible; however, when the surgery is performed, the tightness of the muscles around the incision restrict the size of the operative field or obstruct the operation of the surgical instruments. Please refer to FIG. 1 and FIG. 2. In a minimally invasive surgery, an extending member or sleeve is usually provided to maintain the operative path. Specifically, the surgery is performed via small incisions on the back of the patient corresponding to the positions of pedicles on the two sides of the vertebral process. The pedicle screw 9 (9a) provided with the extending members 7 or the sleeve 8 is implanted in the vertebral body to maintain the operative path such that the surgical instruments can be operated on the pedicle screw 9 (9a) with a sufficient operative field and no obstruction to finish the installation of the pedicle screw fixation system.

FIG. 1 illustrates a schematic view of a conventional pedicle screw having two extending members. As shown in FIG. 1, a pedicle screw 9 of this type includes a screw shaft 91 and a receiver 92. The extending members 7 are connected to the top end of the receiver 92. The receiver 92 is formed in a U shape with two arms 921. The pedicle screw 9 is disposed on the top of the arm 921 of the receiver 92 to form an engaging structure 93, and the two extending members 7 are inserted into the engaging structure 93. After the pedicle screw 9 having the extending members 7 is fixed on the vertebral body of the patient, the muscle tissue can be held by the extending members 7, forming a channel for maintaining the operative field and for the surgical instruments to approach the pedicle screw 9.

As shown in FIG. 2, the pedicle screw 9a of this type also includes a screw shaft 91a and a receiver 92a. The front end of the sleeve 8 has a clamping portion 81 for directly clamping or being sleeved on the outside the arm 921a of the receiver 92a. Similarly, after the pedicle screw 9a having the sleeve 8 is implanted into the vertebral body of the patient, the muscle tissue can be held by the sleeve 8.

However, the extending members 7 in FIG. 1 are connected to the receiver 92 only by the engaging structure 93. In FIG. 2, the sleeve 8 is directly clamped or sleeved on the arms 921 of the receiver 92a. The stability of the connection mechanism is such that if an external force is applied on the connection mechanism, the extending members 7 or the sleeve 8 can easily slip, be skewed, or even be dislodged. Although manufacturers are currently attempting to improve the connection stability of the extending members 7 and the arm 921 by increasing and deepening the size of the engagement structure 93 or other designs, the specially-designed or enlarged extending members 7 and the sleeve 8 clamped or sleeved on the arms 921, 921a of the receiver 92, 92a will increase the overall outer diameter of the pedicle screw 9, 9a after installation and expand the incision, which is contractionary to the original goal of minimally invasive surgery.

In detail, since the upper edge space of the arm 921 of the pedicle screw 9 is quite limited, in order to dispose the engaging structure 93, it is necessary to increase the wall thickness of the arm 921 and thereby to increase the outer diameter of the receiver 92. As for the sleeve 8 having a tubular shape, when it is directly clamped or engaged with the outside of the receiver 92a, the outer diameter of the joint where the upper edge of the receiver 92a is connected with the sleeve 8 will inevitably be increased greatly.

Therefore, it is important in minimally invasive spinal surgery to maintain a stable connection of the extending members (or the sleeve) with the implanted screw and effectively limit the expansion of the outer diameter of the joint.

SUMMARY OF THE INVENTION

In view of the above problems, it is an object of the present invention to provide a device for stabilization of bone segment and an extending assembly thereof. The device includes a screw assembly, two supporting members and two extending members. The supporting members are connected to the receiver of the screw assembly, the extending member can pass through the supporting member to be connected to the receiver, the connection between the extending member and the screw assembly is more stable with the supporting member, and the outer diameter of the device at the connection position is not substantially increased comparing to the outer diameter of the individual screw assembly.

In order to achieve the above object, the present invention provides a device for stabilization of bone segment. The device includes a screw assembly, two supporting members and two extending members. The screw assembly includes a receiver and an anchoring member. The receiver has a retainer and two opposite arms extending along the longitudinal axis of the device from positions adjacent to the retainer. The anchoring member is connected to the retainer. The two supporting members are connected to the two arms and respectively extend along the longitudinal axis. The two extending members each have a through hole, wherein the extending members are connected to the two arms with the supporting members passing through the respective through holes.

In order to achieve the above object, the present invention further provides an extending assembly for use in a device for stabilization of bone segment. The device includes a screw assembly, two supporting members and two extending members. The screw assembly includes a receiver having a retainer and two opposite arms extending along the longitudinal axis of the device from positions adjacent to the retainer. The two supporting members are connected to the two arms and respectively extend along the longitudinal axis. The two extending members each have a through hole, wherein the extending members are connected to the two arms with the supporting members passing through the respective through holes.

According to an embodiment of the present invention, the supporting member has an external thread at one connecting end, and a top surface of the arm has a concave portion having an internal thread corresponding to the external thread, and the supporting member is screwed and locked to the arm.

According to an embodiment of the present invention, the extending member has a recess at an end connected to the arm, and the recess engages an outside portion of the arm.

According to an embodiment of the present invention, the through hole is located at the bottom of the recess; after the supporting member passes through the through hole, the extending member is engaged with the outside portion of the arm through the recess to be connected with the arm.

According to an embodiment of the present invention, the recess communicates with the outside through the bottom of the extending member and a side connected to the bottom thereof.

According to an embodiment of the present invention, the extending member has a supporting member retaining structure disposed thereon to restrict the movement of the supporting member corresponding to the extending member.

According to an embodiment of the present invention, the extending member has a retaining hole communicating with the through hole and the outer space; the supporting member retaining structure is disposed adjacent to the retaining hole and has a pressing portion for pressing the supporting member through the retaining hole.

According to an embodiment of the present invention, the supporting member retaining structure is pivotally connected to the extending member, and the pressing portion has a plane; after the supporting member retaining structure is rotated, the plane presses the supporting member.

According to an embodiment of the present invention, the arm has a first thickness, and the extending member has a second thickness at a junction formed after the extending member is connected to the arm; a difference between the first thickness and the second thickness is between 0.25 mm and 1 mm.

According to an embodiment of the present invention, the arm has a first thickness, and the extending member has a second thickness at a junction formed after the extending member is connected to the arm; a difference between the first thickness and the second thickness is between 0.2 mm and 0.5 mm.

According to an embodiment of the present invention, the difference between the first thickness and the second thickness is substantially the thickness of the extending member at the end connected to the arm.

According to an embodiment of the present invention, the extending member comprises a fastener; the fastener has an engagement slot for engaging with the two extending members at a top end simultaneously.

According to an embodiment of the present invention, the fastener further has two grooves, which are respectively communicated with the engaging slot, and the two supporting members are respectively disposed to pass through the two grooves.

According to an embodiment of the present invention, the device for stabilization of bone segment is used in a minimally invasive spinal surgery.

As described above, the present invention provides a device for stabilization of bone segment and an extending assembly thereof. The device includes a screw assembly and two supporting members, and the supporting members are connected to the two arms of the receiver. The extending assembly has two extending members, each having a through hole. The supporting member passes through the through hole of the extending member, and the bottom end of the extending member is connected to the arm of the receiver. Therefore, the supporting member can be used as the supporting backbone of the extending member to provide a solid foundation, stabilizing the position of the extending member to avoid swinging and displacement and thereby improving the connection stability of the extending member and the arm. During operation, the extending members on both sides will not be skewed or dislodged when subjected to an external force. With this structural design, it can achieve the same stability requirement by using a smaller structure at the connection position of the extending members and the arms; for example, the upper edge of the arm is not required to be additionally thickened for disposing a larger recess, thereby avoiding an increase in the size of the screw and an enlarged surgical wound subsequently.

In addition, in an embodiment of the present invention, the extending member passes through the supporting member to be connected to the arm such that the extending member can be directly removed and reassembled along the fixed direction (for example, the longitudinal axis of the device for stabilization of bone segment). The vertebrae of spinal column from a particular bending angle, especially the five lumbar vertebrae, which form a convex curvature to the abdomen. For example, in the operation for correcting the L5 and S1 vertebrae, the traditional minimally invasive surgery sometimes has the problem of staggering conflicts of extending members. With the implementation of the present invention, if a conflict occurs, one of the extending members can be easily removed along the fixed direction such that the insertion angle of the screw will not be compromised due to the conflict of the extending members. It can also avoid expansion or pulling of the incision during the removal and reassembly (depending on surgery requirements) of the extending members; meanwhile, the supporting member can still temporarily and partially maintain the incision size when the extending member is removed to provide a clear operative field.

DETAILED DESCRIPTION OF THE PREFERRED EMBODIMENT

In order to make the structure and characteristics as well as the effectiveness of the present invention to be further understood and recognized, the detailed description of the present invention is provided as follows along with embodiments and accompanying figures.

First, the device for stabilization of bone segment in the present invention is described using the embodiment of a pedicle screw of a pedicle screw fixation system used in minimally invasive spinal surgery as an example. But it should be known to those skilled in the art that the device of the present invention is not limited to the pedicle screw.

Figure 3:
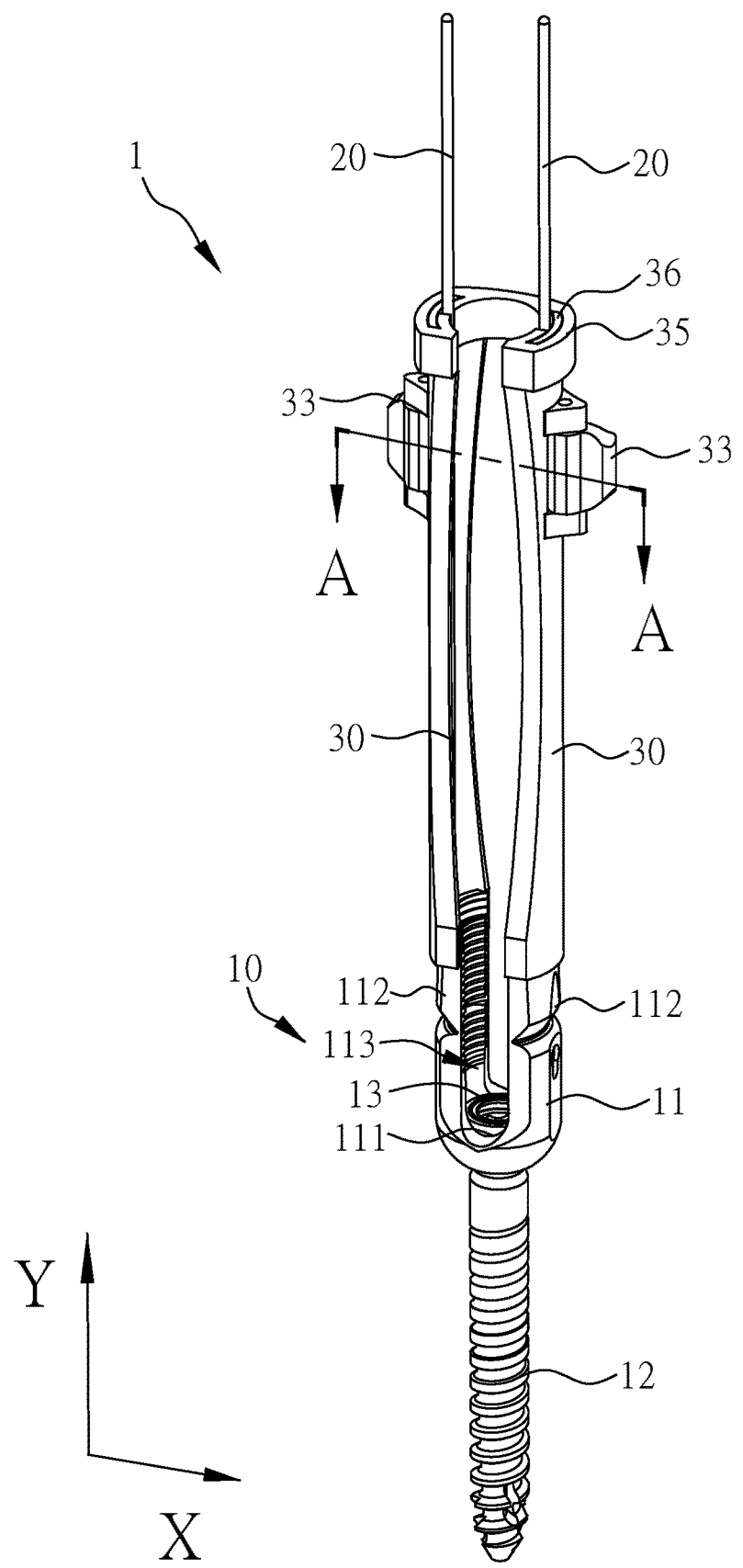
FIG. 3 illustrates a schematic view of an embodiment of a device for stabilization of bone segment in the present invention.
Figure 4:
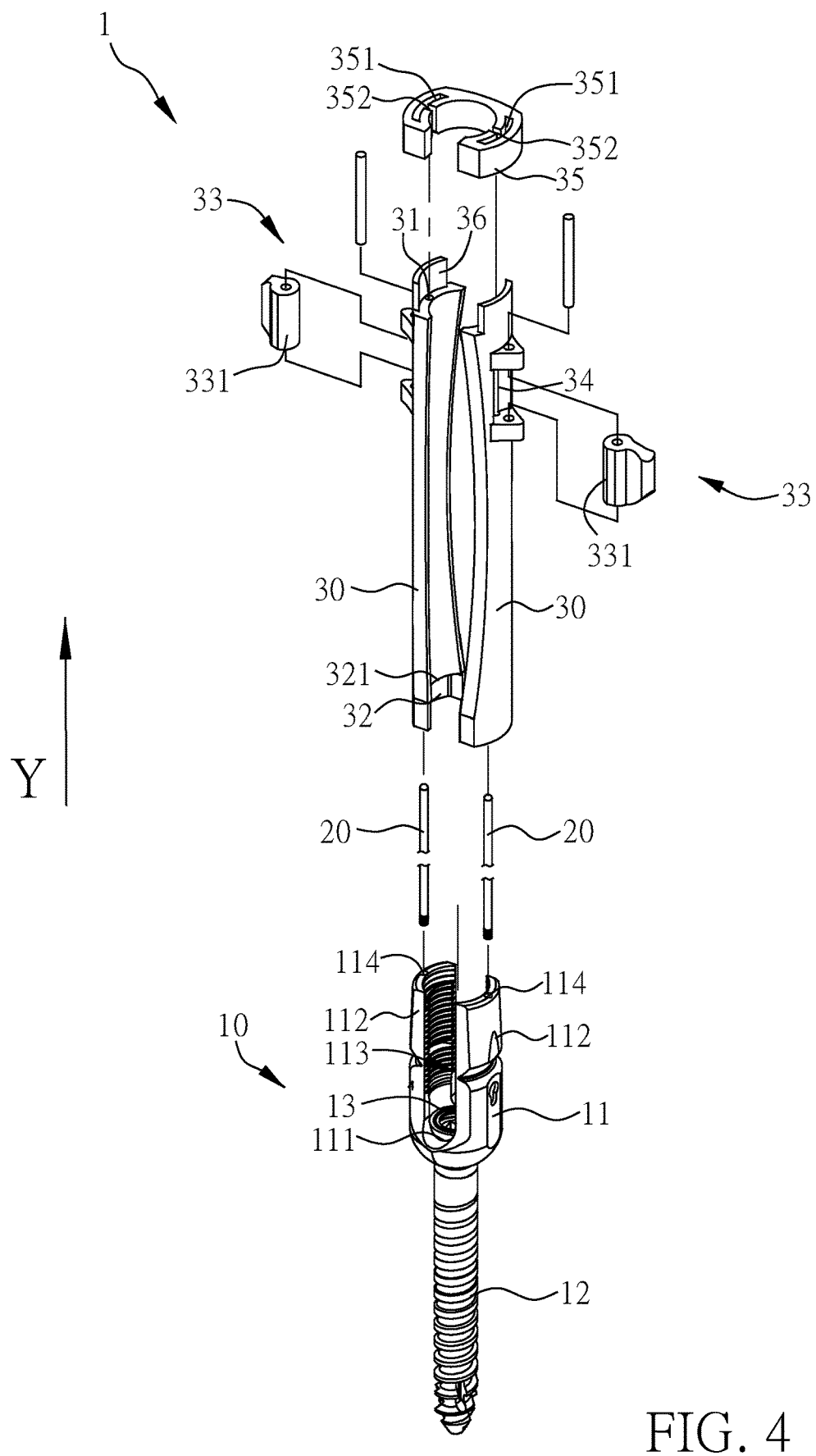
FIG. 4 illustrates an explosive view of the device for stabilization of bone segment shown in FIG. 3.

As shown in both FIG. 3 and FIG. 4. FIG. 3 illustrates a schematic view of an embodiment of a device for stabilization of bone segment in the present invention, and FIG. 4 illustrates an explosive view of the device for stabilization of bone segment shown in FIG. 3. In this embodiment, the device for stabilization of bone segment (hereinafter referred to as device 1) includes a screw assembly 10, two supporting members 20 and two extending members 30. The screw assembly 10 of this embodiment is one of the pedicle screws used in the pedicle screw fixation system, and the supporting members 20 and the extending members 30 are mounted on the screw assembly 10.

Spinal disorders occur most often in the lumbar spine, especially at the L4-L5 vertebral level where the pedicle screw fixation system is often performed. In the first step, the surgeon has to create a screw channel by using an instrument such as an awl to create an entry point on the lumbar vertebrae and then bore through a pedicle to the cancellous bone of the vertebra. Then the surgeon can choose whether to expand or tap the screw channel to prepare for screw implantation. After the creation of the screw channel, the device 1 of the embodiment is assembled by the surgeon on the exterior of the patient's body. For example, after the screw assembly 10 is assembled, the supporting members 20 and the extending members 30 are mounted on the screw assembly 10. After the device 1 is assembled, it is implanted on the vertebral body; that is, the screw assembly 10 with the supporting members 20 and the extending members 30 are implanted together on the vertebral body. The detailed structures of the screw assembly 10, the supporting members 20 and the extending members 30, as well as their connection relationship and assembly sequence, will be described below.

The screw assembly 10 of this embodiment includes a receiver 11 and an anchoring member 12. The receiver 11 is usually formed in a U shape and thus may be referred to as a U-shaped head. The receiver 11 has a retainer 111 and two opposite arms 112. The retainer 111 is located in the recess of the receiver 11, and the two opposite arms 112 extend toward the longitudinal axis Y of the device 1 from positions adjacent to both sides of the retainer 111. The retainer 111 and the arms 112 jointly form an accommodating space 113 for accommodating spinal surgery accessories, such as a connecting rod and a locking screw fastening the connecting rod used in the pedicle screw fixation system. In addition to accommodating the connecting rod and locking screw, the accommodating space 113 is an entry for operating various spinal surgical instruments on the screw assembly 10.

Figure 6A:
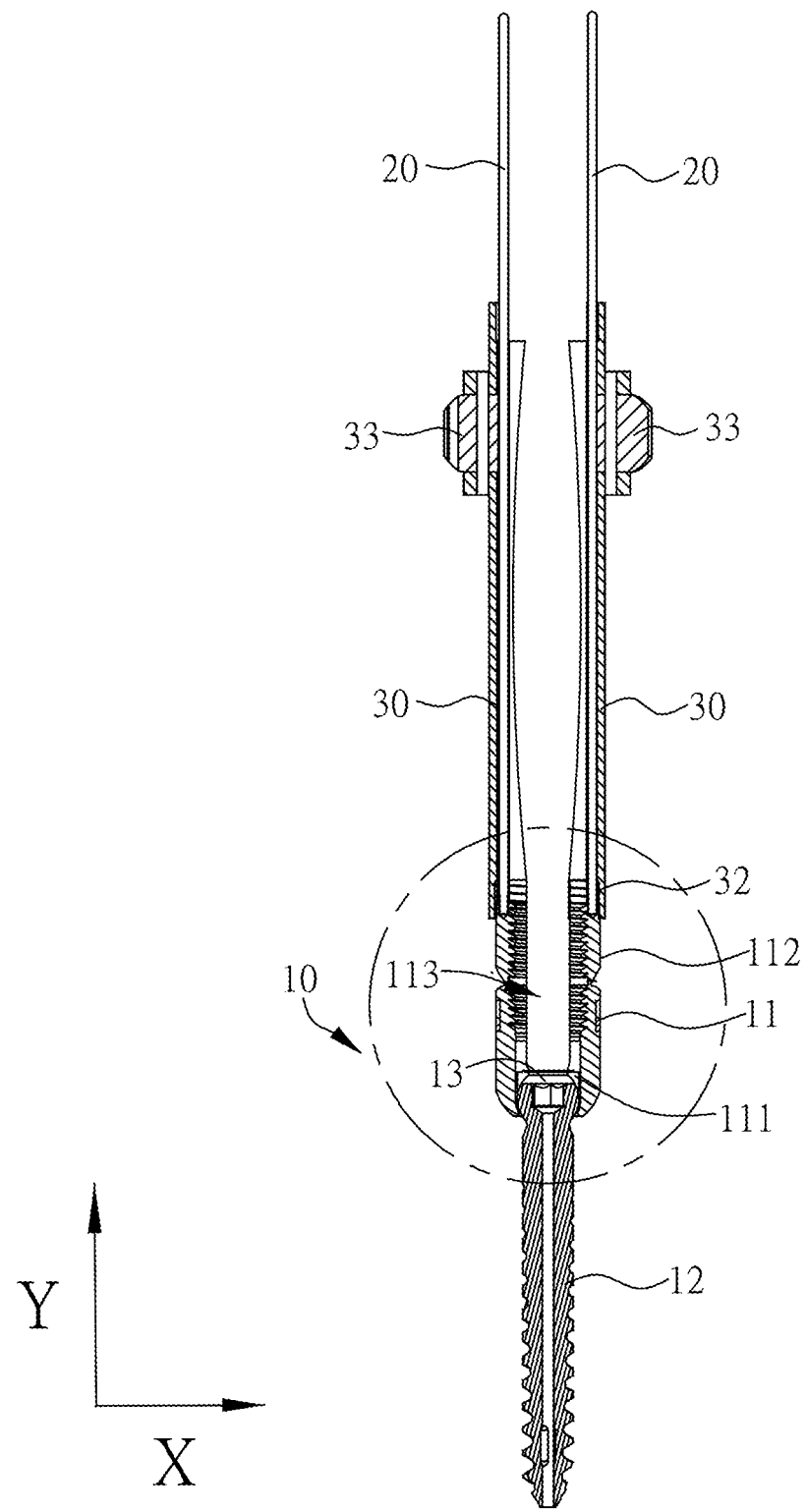
FIG. 6A illustrates a cross-sectional view of the device for stabilization of bone segment shown in FIG. 5C.
Figure 6B:
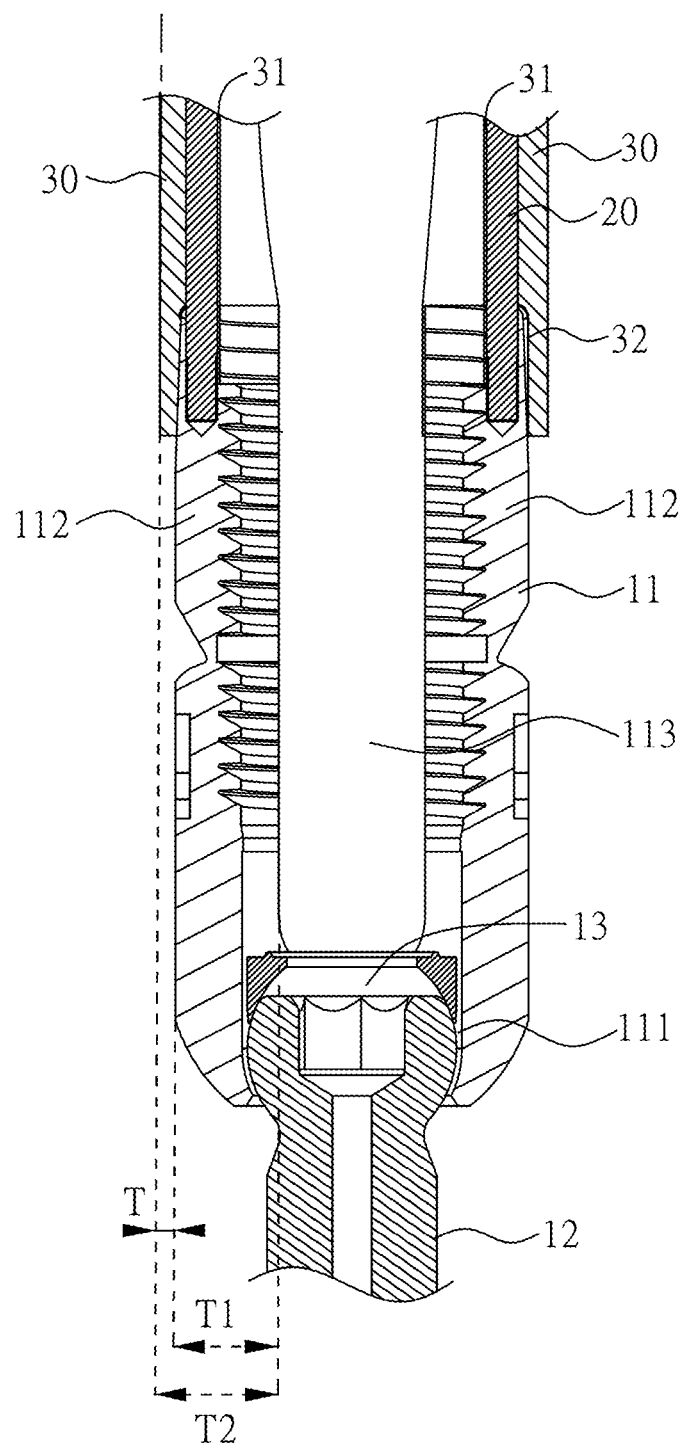
FIG. 6B illustrates an enlarged view of the circled area shown in FIG. 6A.

The anchoring member 12 of the present embodiment is a screw shaft, and the anchoring member 12 is connected to the retainer 111. The anchoring member 12 and the receiver 11 can be integrally formed or connected by a spherical joint (as shown in FIG. 6A or FIG. 6B). In terms of commercial products, the former is called a single-axis screw or monoaxial screw, and the latter is called a multi-axial, universal or polyaxial screw. This embodiment is an example of a polyaxial screw connected by a spherical joint. The structure of the screw assembly 10 is briefly described below.

The anchoring member 12 of this embodiment has a spherical head, and the retainer 111 is a through hole. The spherical head of the anchoring member 12 is accommodated in the retainer 111. During assembly of the screw assembly 10, the anchoring member 12 is first passed through the accommodating space 113 and the retainer 111; the diameter of the spherical head of the anchoring member 12 is greater than the inner diameter of the retainer 111, so the anchoring member 12 is limited in the retainer 111. Preferably, the screw assembly 10 further has an inner cap 13. The inner cap 13 is placed on the spherical head of the anchoring member 12, and then the spherical head of the anchoring member 12 and the inner cap 13 are pressed into the retainer 111 together for fixation to the retainer 111 by a jig. In addition, a thread on the anchoring member 12 can be customized depending on the location of the implantation. Pedicle screw is the one type of the screws with a shaft having the same pitches evenly distributed on its body. Cortical screw is the other type with a shaft having a tread formed with shorter pitches in the upper portion and longer pitches in the lower portion. However, the present invention is not limited to any type of the screws mentioned herein. In addition, the general definition of a minimally invasive spinal surgery is that a single surgical incision is no greater than three centimeters. According to the definition, both the pedicle screw and cortical screw can be implemented in minimally invasive spinal surgeries.

Figure 5A:
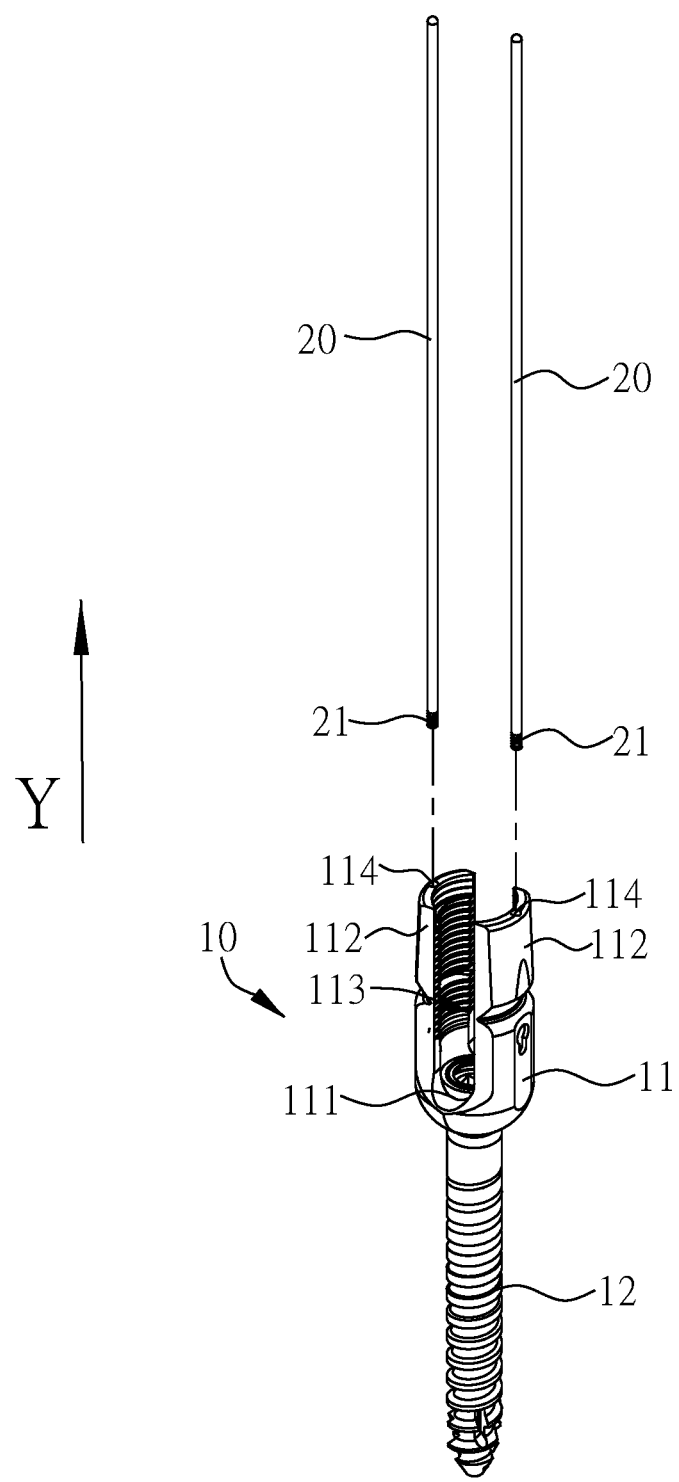
FIG. 5A illustrates a schematic view of the supporting members of FIG. 4 before assembly to the screw assembly.

As shown in FIG. 5A, which illustrates a schematic view of the supporting members of FIG. 4 before connected to the screw assembly. After assembly of the screw assembly 10, the two supporting members 20 are respectively connected to the two arms 112, and the supporting members 20 extend in the same direction of the longitudinal axis Y as the two arms 112. In this embodiment, the supporting member 20 is assembled on the top surface of the arm 112 of the receiver 11 such that the supporting member 20 is extending along the longitudinal axis Y toward a direction away from the anchoring member 12. Moreover, the supporting member 20 and the receiver 11 can be integrally formed or can be connected in detachable manners. The supporting members 20 and the receiver 11 are connected in a screwed manner in this embodiment. Preferably, the supporting member 20 has an external thread 21 at one connecting end, and the top surface of the arm 112 has a concave portion 114 preferably located in the middle of the top surface of the arm 112, and the concave portion 114 has an internal thread corresponding to the external thread 21 so that the supporting member 20 can be connected to the arm 112 in the screwed manner. Preferably, the supporting member 20 is configured to be a long rod structure, a length of the supporting member 20 is about 7 to 20 cm, preferably 10 to 15 cm, and a diameter of the supporting member 20 is about 0.2 cm or less, preferably 0.1 to 0.2 cm. Moreover, the supporting member 20 can be made of various biocompatible and rigid materials, such as titanium.

Figure 5B:
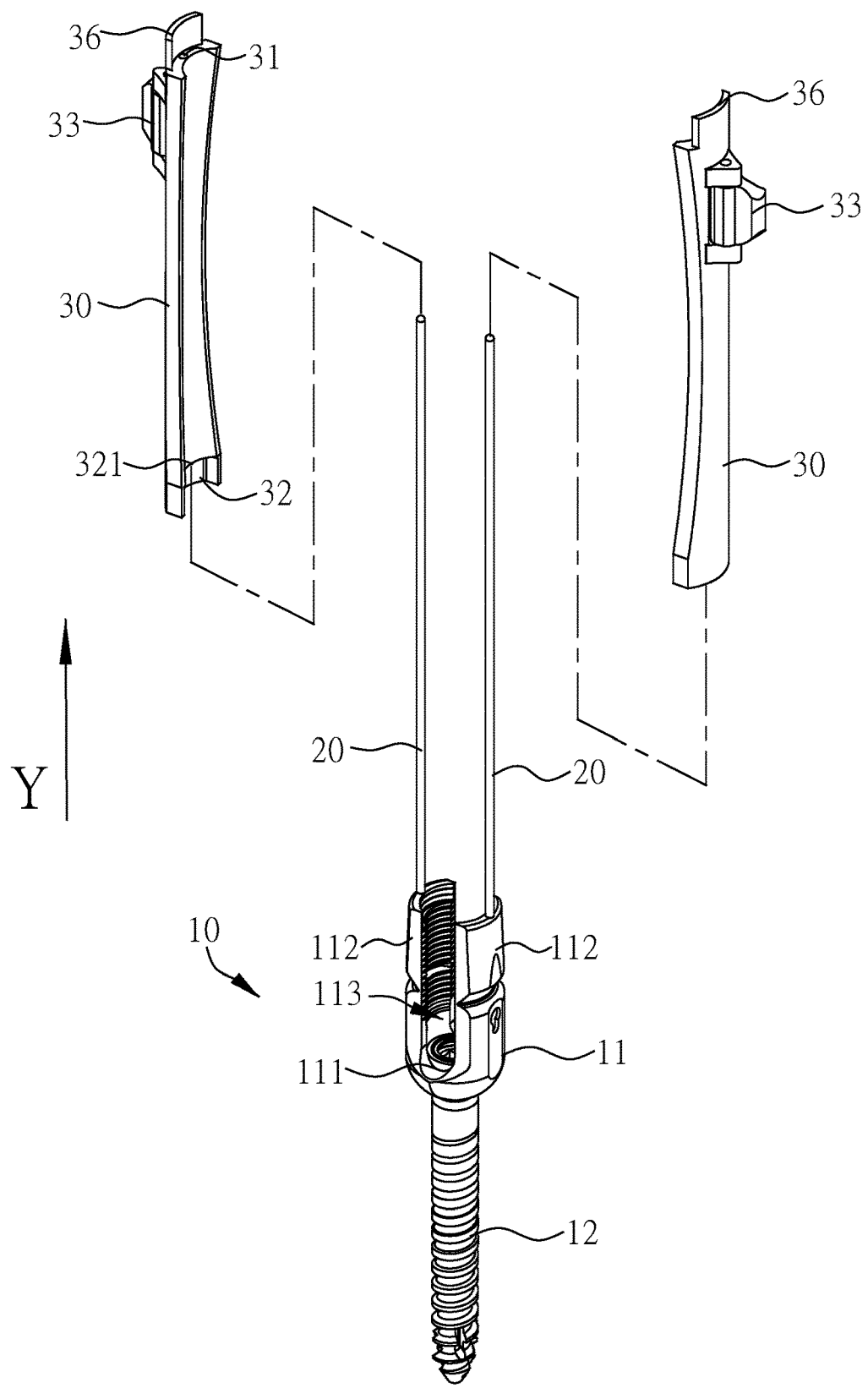
FIG. 5B illustrates a schematic view of the extending members of FIG. 4 before assembly to the screw assembly.
Figure 5C:
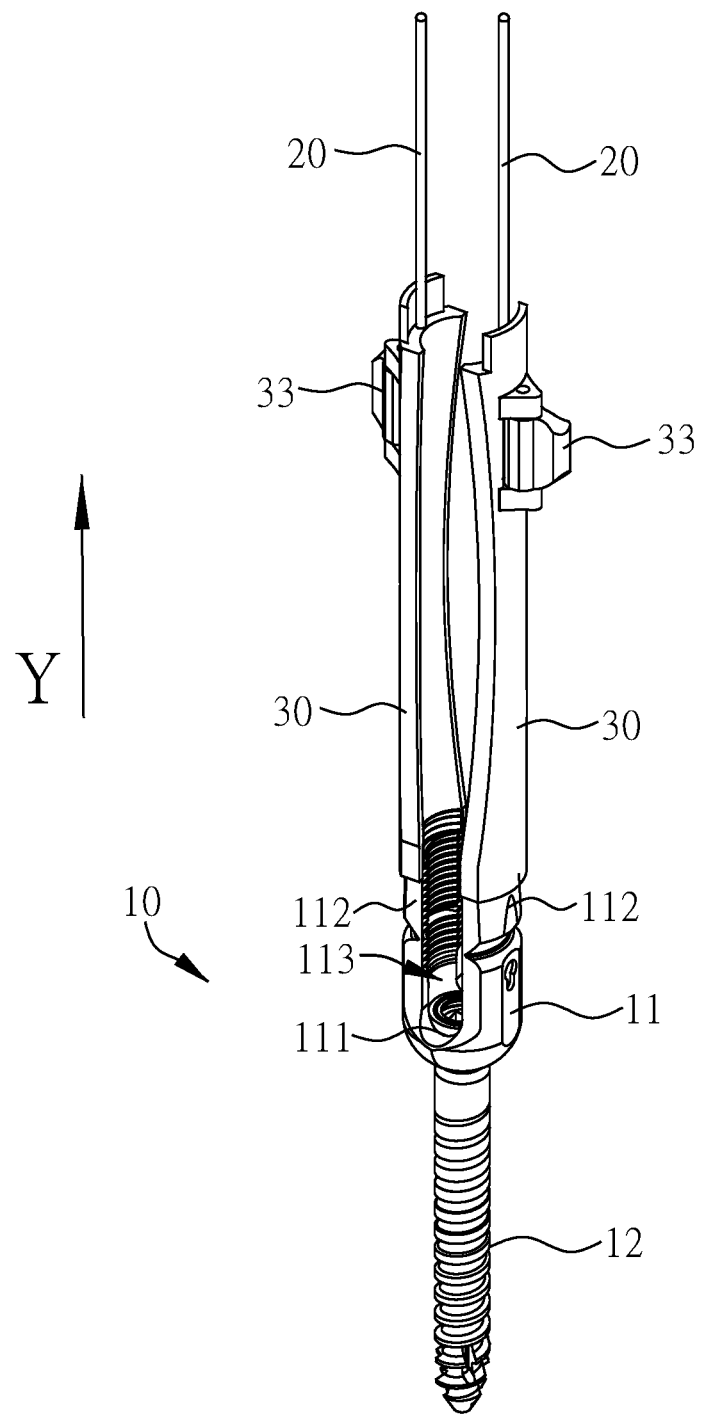
FIG. 5C illustrates a schematic view of the extending members of FIG. 4 after assembly to the screw assembly.

As shown in FIG. 5B and FIG. 5C. FIG. 5B illustrates a schematic view of the extending members of FIG. 4 before connected to the screw assembly; and FIG. 5C illustrates a schematic view of the extending members of FIG. 4 after connected to the screw assembly. Once the supporting member 20 has been connected to the arm 112 of the receiver 11 in the screwed manner, as shown in FIG. 5B, the extending member 30 is then connected to the screw assembly 10. In this embodiment, each of the two extending members 30 have a through hole 31 respectively. The surgeon can make the two supporting members 20 pass through the through holes 31 of the extending members 30 respectively such that the extending members 30 pass over the supporting members 20 and the bottom end of the individual extending members 30 can be connected to the arm 112, as shown in FIG. 5C. The supporting member 20 of the present embodiment has a shape corresponding to that of the arm 112. For example, both of the supporting member 20 and the arms 112 are formed in arc-shaped structures, and the through hole 31 is located in the middle of the extending member 30. When the extending member 30 passes over the supporting member 20 via the through hole 31, it can reach and be connected to the top surface of the arm 112.

As described above, the operating end of the surgical instrument functions in the accommodating space 113, defined by the retainer 111 and the arm 112. Once the device 1 is assembled and implanted within the vertebral body, the extending members 30 connected to the arm 112 provide a function of holding the muscle tissue to maintaining a channel (operative path) directly communicating to the accommodating space 113. The surgeon can pass different surgical instruments through the channel defined by the extending members 30 and reach the accommodating space 113 to perform the surgery.

Figure 1:
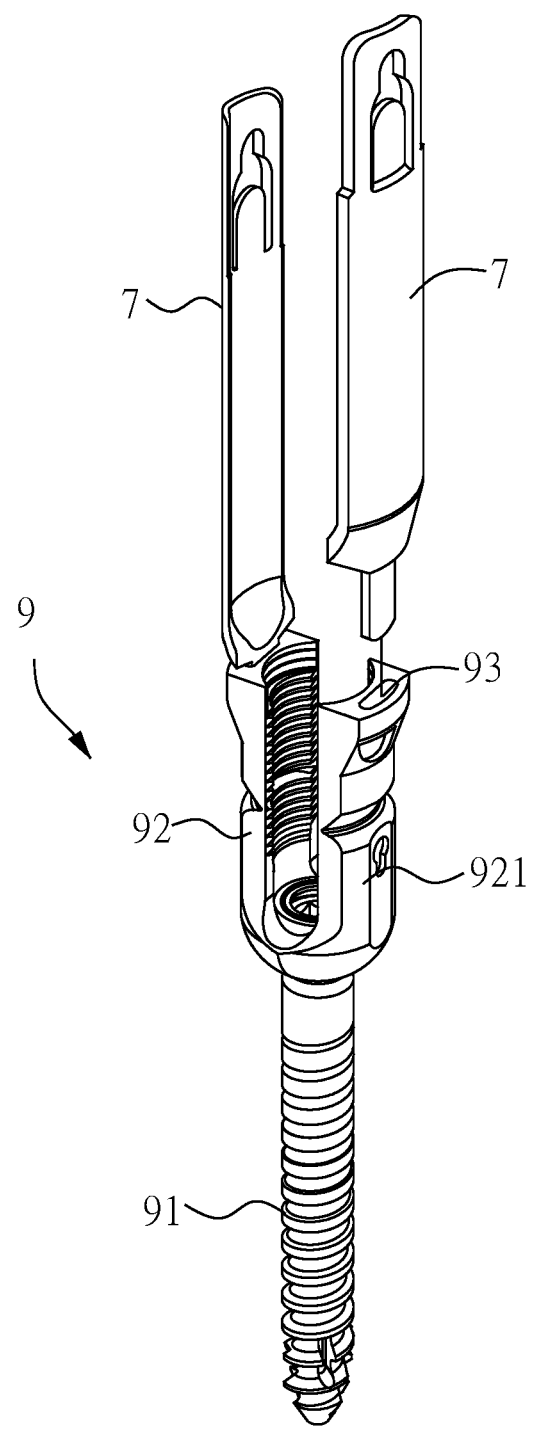
FIG. 1 illustrates a schematic view of a conventional pedicle screw having extending members.
Figure 2:
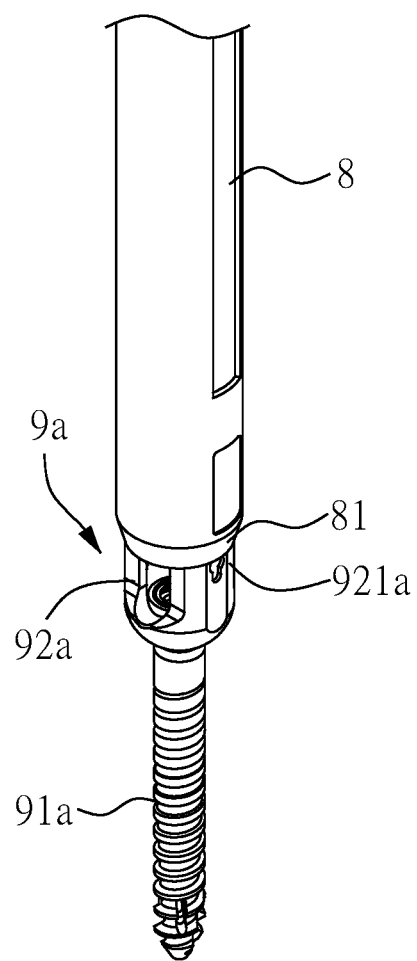
FIG. 2 illustrates a schematic view of a conventional pedicle screw having a sleeve.

According to the structure described above, the supporting member 20 can be considered as the supporting backbone of the extending member 30, which can perform a function of effectively improving the stability of the connection between the extending member 30 and the arm 112 as a ground pile. Since the device 1 is a small implant, in general, the structure of the extending member 30 and the arm 112 cannot be too complicated or large. Therefore, the conventional structure that the extending member and the arm are connected by manners of mortise-and-tenon structure (as shown in FIG. 1), sleeving the extending member on the arm (as shown in FIG. 2), or sleeving the arm on the extending member is often used. However, due to the limitation of the available space, the structure for mortise-and-tenon or sleeve usually can only be designed to use a very shallow recess, therefore, provide a quite limited function for stabling the connection. When the upper end of the extending member 30 is subjected to an external force, the extending member 30 is easily skewed or fallen off. However, in this embodiment, by the supporting force provided by the supporting member 20, only a simple engagement or a mortise-and-tenon structure is required to stabilize the connection between the extending member 30 and the arm 112 (even if the depth of the recess is still shallow). The extending member 30 can be stably fastened to the arm 112 of the receiver 11 to prevent being skewed or dislodged by an external force during the surgery. Specifically, the top surface of the arm 112 can be provided with a convex portion, and the bottom surface of the extending member 30 (refer to the surface connected to the arm 112) can be provided with a concave portion; likewise, the top surface of the 112 is provided with a concave portion, and a convex portion is disposed corresponding to the bottom surface of the extending member 30.

Preferably, the extending member 30 of this embodiment is connected to the arm 112 by a recess 32. In detail, the extending member 30 has a recess 32 at one end connected to the arm 112; that is, the bottom end of the extending member 30 has a recess 32. In this embodiment, the end of the extending member 30 adjacent to the receiver 11 is referred to as the bottom end, and the end away from the receiver 11 is referred to as the top end. The recess 32 of this embodiment communicates with the outside through the bottom end of the extending member 30 and one side connected to the bottom end thereof. In other words, the recess 32 has two sides which are open and can be communicated with the outside, where one side is the bottom end surface of the extending member 30 and the other side is the side connected to the bottom end and is also the side facing the other extending member 30. According to this structure, the recess 32 can be engaged with the arm 112 on the outside. When the recess 32 is engaged with the arm 112 at the outside portion of the arm 112, the connection between the recess 32 and the arm 112 is completed.

As shown in FIG. 5B, FIG. 6A and FIG. 6B, FIG. 6A illustrates a cross-sectional view of the device for stabilization of bone segment shown in FIG. 5C, and FIG. 6B illustrates an enlarged view of the circled area shown in FIG. 6A. The through hole 31 is formed in a long passage shape. One end of the through hole is located at the top end of the extending member 30, and the other end is located at the bottom end of the extending member 30. In this embodiment, it is located at the bottom of the recess 32, as shown in FIG. 6B. After the extending member 30 is sleeved on the supporting member 20 with the through hole 31, the extending member 30 moves toward the arm 112 along the longitudinal axis Y with the supporting member 20 being the axis. Finally, the extending member 30 reaches and is connected to the arm 112 by sleeving the recess 32 on the outside portion of the arm 112. It should be noted that since the supporting member 20 is disposed in the through hole 31, the through hole 31 of FIG. 6B is illustrated between the inner wall of the through hole 31 and the supporting member 20. Furthermore, in this embodiment, the extending member 30 can be connected to the arm 112 through the recess 32, and the recess 32 is designed to be communicated with the outside through the bottom end of the extending member 30 and the side connected to the bottom end thereof; that is, the bottom of the extending member 30 is an open recess, rather than a pit only having a bottom opening (shown in the figures). Furthermore, the supporting member 20 is used for providing support to the extending member 30 to prevent the extending member 30 from being displaced or rotated toward the horizontal axis when the extending member 30 is subjected to external stress. The advantage of the extending member 30 using the recess 32 instead of the pit to be connected to the arm 112 is that the thickness T of the end of the extending member 30 can be reduced, thereby addressing the problem that larger extending member 30 has a very high chance to expand or tear the surgical incision during surgery. Specifically, since the size of the extending member 30 at the bottom end is limited, if a pit for accommodating the arm 112 has to been formed at this position, it is unavoidable to use an extending member 30 having a larger thickness at the bottom end.

As shown in FIG. 6B, the arm 112 of the receiver 11 of this embodiment has a first thickness T1. When the recess 32 of the extending member 30 is sleeved on the outside portion of the arm 112, a second thickness T2 is defined at the junction of the extending member 30 and arm 112; that is, the second thickness T2 is the sum of the thickness T of the extending member 30 protruding from the arm 112 and the first thickness T1 of the arm 112. The difference between the first thickness T1 and the second thickness T2 is substantially between 0.25 mm and 1 mm, preferably between 0.2 mm and 0.5 mm. In other words, in this embodiment, the thickness of the extending member 30 protruding from the arm 112 is preferably between 0.25 mm and 1 mm, and more preferably between 0.2 mm and 0.5 mm.

After the supporting member 20 passes through the through hole 31 of the extending member 30, the extending member 30 can be connected to the arm 112 by using the supporting member 20 as a backbone; therefore, the supporting member 20 acts as the supporting structure of the extending member 30, while the recess 32 of the extending member 30 is provided for retaining the extending member 30, so the thickness of the extending member 30 protruding from the arm 112 can be greatly reduced. In an embodiment, the thickness T of the extending member 30 at the recess 32 can be reduced to only 0.2 mm and still can achieve the goal of firmly connecting the extending member 30 to the arm 112. Compared with the extending members 7 and the sleeve 8 in the prior arts, this embodiment can simplify the structure of the junction (the position where the extending member 30 is connected to the arm 112 of the receiver 11) and reduce the thickness thereof. The size of the surgical wound can be reduced as well.

As shown in FIG. 3, FIG. 4 and FIG. 6A, preferably, the extending member 30 of this embodiment has a supporting member retaining structure 33. The supporting member retaining structure 33 is disposed on the extending member 30 to restrict the movement of the supporting member 20 corresponding to the extending member 30 along the longitudinal axis Y, or to restrict the rotation of the extending member 30 corresponding to the supporting member 20 in order to prevent the recess 32 of the extending member 30 from separating from the arm 112 or otherwise becoming loose or disengaged. In other words, that the extending member 30 of this embodiment is engaged with the outside portion of the arm 112 through the recess 32 prevents the extending member 30 from rotation relative to the arm 112. In addition, the supporting member retaining structure 33 restricts the movement of the extending member 30 corresponding to the supporting member 20, or the displacement of the supporting member 20 within the through hole 31 resulting in a lower possibility of separation of the extending member 30 from the arm 112.

Figure 7A:
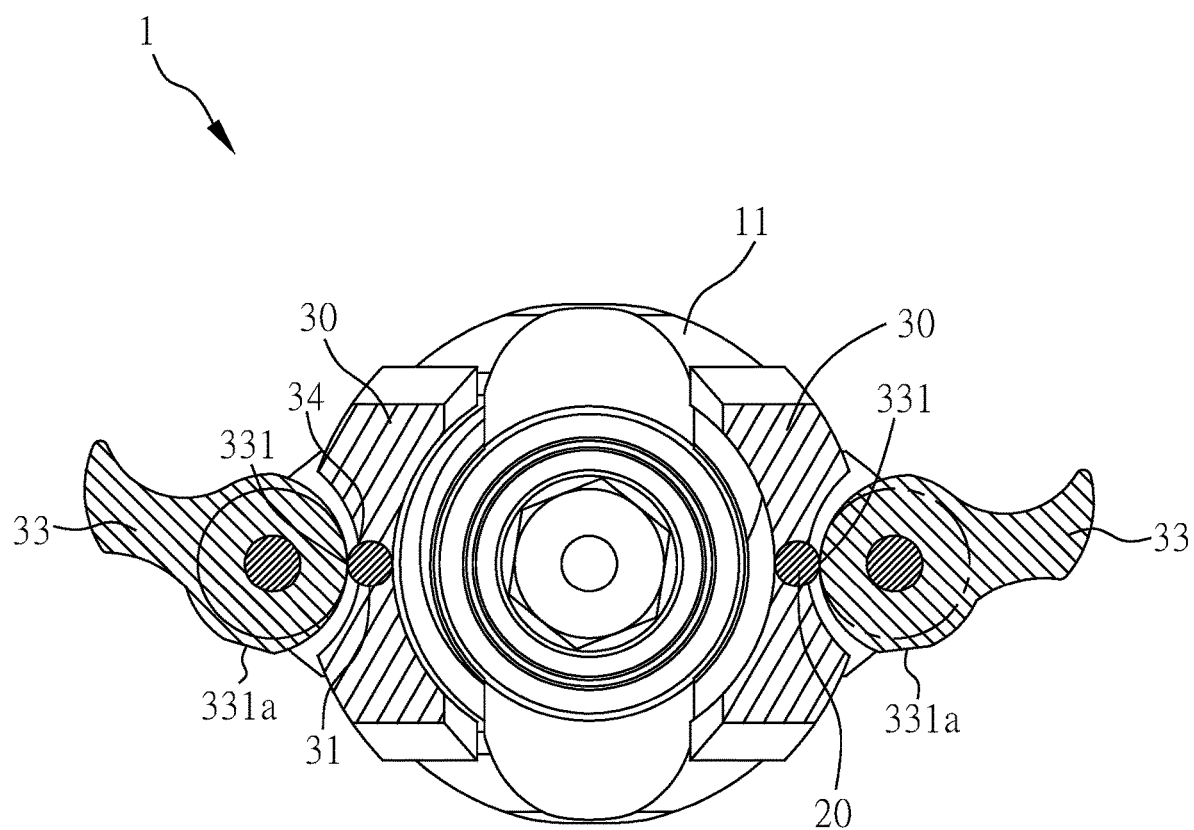
FIG. 7A illustrates a cross-sectional view of the A-A line shown in FIG. 3.

FIG. 7A illustrates a cross-sectional view of the A-A line shown in FIG. 3. As shown in FIG. 4 and FIG. 7A, the extending member 30 of this embodiment has a retaining hole 34 that communicates with the through hole 31 and the outer space. It is noted that since the retaining hole 34 communicates with the through hole 31, the retaining hole 34 shown in FIG. 7A is illustrated on the arc surface adjacent to the retaining hole 34. In addition, the supporting member retaining structure 33 of this embodiment is disposed adjacent to the retaining hole 34, and the supporting member retaining structure 33 has a pressing portion 331, which press the supporting member 20 through the retaining hole 34, thereby fastening the relative positions of the supporting member 20 and the extending member 30 to prevent the movement of the supporting member 20 corresponding to the extending member 30.

Figure 7B:
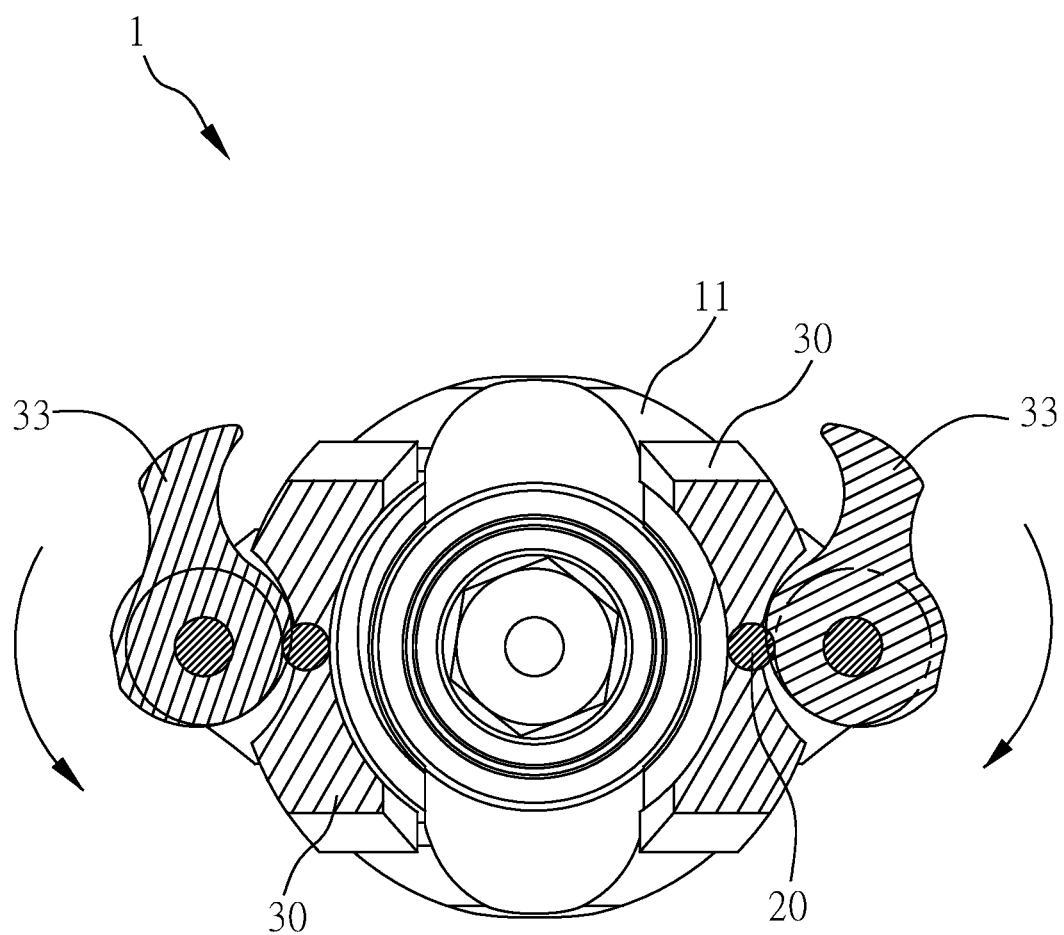
FIG. 7B illustrates a schematic view of the supporting member retaining structure shown in FIG. 7A being rotated.

Preferably, the supporting member retaining structure 33 is pivotally connected to the extending member 30, and the pressing portion 331 of the supporting member retaining structure 33 has a plane 331a. The circumference of the retaining hole 34 of this embodiment is a curved surface functioning to accommodate the pressing portion 331. When the supporting member retaining structure 33 is rotated, the plane 331a can press the supporting member 20, as shown in FIG. 7B illustrating a schematic view of the supporting member retaining structure shown in FIG. 7A being rotated. In this embodiment, the plane 331a is designed to occur interference with the supporting member 20 such that when the supporting member retaining structure 33 is rotated, the plane 331a not only press the supporting member 20 but also further forces the supporting member 20 into the through hole 31 to fix the relative positions of the supporting member 20 and the extending member 30.

In other embodiments of the invention, the supporting member retaining structure 33 can also be a nut or other similar elements. Due to the thread is formed at the upper end of the supporting member 20, the position of the thread can still maintain higher than the extending member 30 after the extending member 30 passes through the supporting member 20. Therefore, the extending member 30 and the arm 112 can be firmly fastened together by tightening the supporting member retaining structure 33 along with the thread on the supporting member 20. It is effective to avoid the displacement or swinging of the extending member 30 and thereby stabilize the relative positions of the supporting member 20 and the extending member 30.

As shown in FIG. 3 and FIG. 4, preferably, the extending member 30 of this embodiment includes a fastener 35 with at least one engaging slot 351 used to engage with the two opposite extending members 30 at the top end. The fastener 35 of this embodiment is formed in a C shape and has two engaging slots 351 corresponding to the two opposite extending members 30. Preferably, the top end of the extending member 30 has an engaging portion 36 corresponding to the engaging slot 351. The engaging slots 351 can be sleeved on the engaging portions 36 respectively such that the fastener 35 can be firmly engaged with the two opposite extending members 30 at the top end. In other embodiments, the fastener 35 can have only one engaging slot 351 formed in a C-shaped structure. The fastener 35 having the engaging slot 351 in this particular shape can be simultaneously engaged with the two opposite extending members 30 at the top end. Since the fastener 35 is simultaneously engaged with the two opposite extending members 30 at the top end, it can further prevent the extending member 30 from being inwardly tilted or outwardly expanded along the horizontal axis X during the surgery such that the size of the channel (operative path) defined by the two opposite extending members 30 can be maintained.

Preferably, the fastener 35 of this embodiment further has two grooves 352 respectively communicated with the engaging slot 351. When the engaging slot 351 is engaged with two extending members 30 at the top end, the two opposite supporting members 20 passing through the through hole 31 of the extending member 30 are respectively disposed and then limited in the two grooves 352, as shown in FIG. 4. In operation, the fastener 35 can be placed over the device 1 in a way of aligning the grooves 352 to the supporting members 20. After that, the fastener 35 is moved along the supporting members 20 down to the top of the extending members 30. Then the engaging slot 351 is sleeved on the engaging portion 36. As shown in FIG. 3, the assembly of the fasteners 35 is completed after the steps described above.

In general, the surgeon first screws the supporting members 20 to the arms 112 of the receiver 11, as shown in FIG. 5A and FIG. 5B. Then the extending members 30 are passed over the supporting members 20 with the through holes 31. Then the recesses 32 are engaged with the arms 112 of the receiver 11, as shown in FIG. 5C. The supporting members 20 are firmly fixed in the through holes 31 by rotating the supporting member retaining members 33, as shown in FIG. 7B. Finally, the fastener 35 is engaged with the two opposite extending members 30 at the top end to complete the assembly of the device 1. After the device 1 is ready, the surgeon can use an instrument to implant the device 1 on the patient's vertebral body. The device 1 of this embodiment is applied in a minimally invasive spinal surgery for installation of a pedicle screw fixation system. The device 1 is usually used in multiple pairs, such as six or eight pairs, and the devices 1 are implanted within the pedicles of each vertebra from two sides of the spinous processes.

In other embodiments of the present invention, the two extending members 30 and the fastener 35 can be prefabricated as one unit or may be integrally formed into a sleeve-like or arch-shaped structure. It can help the surgeon to skip the steps of assembling the extending members 30 and the fasteners 35 during the surgery.

Figure 8A:
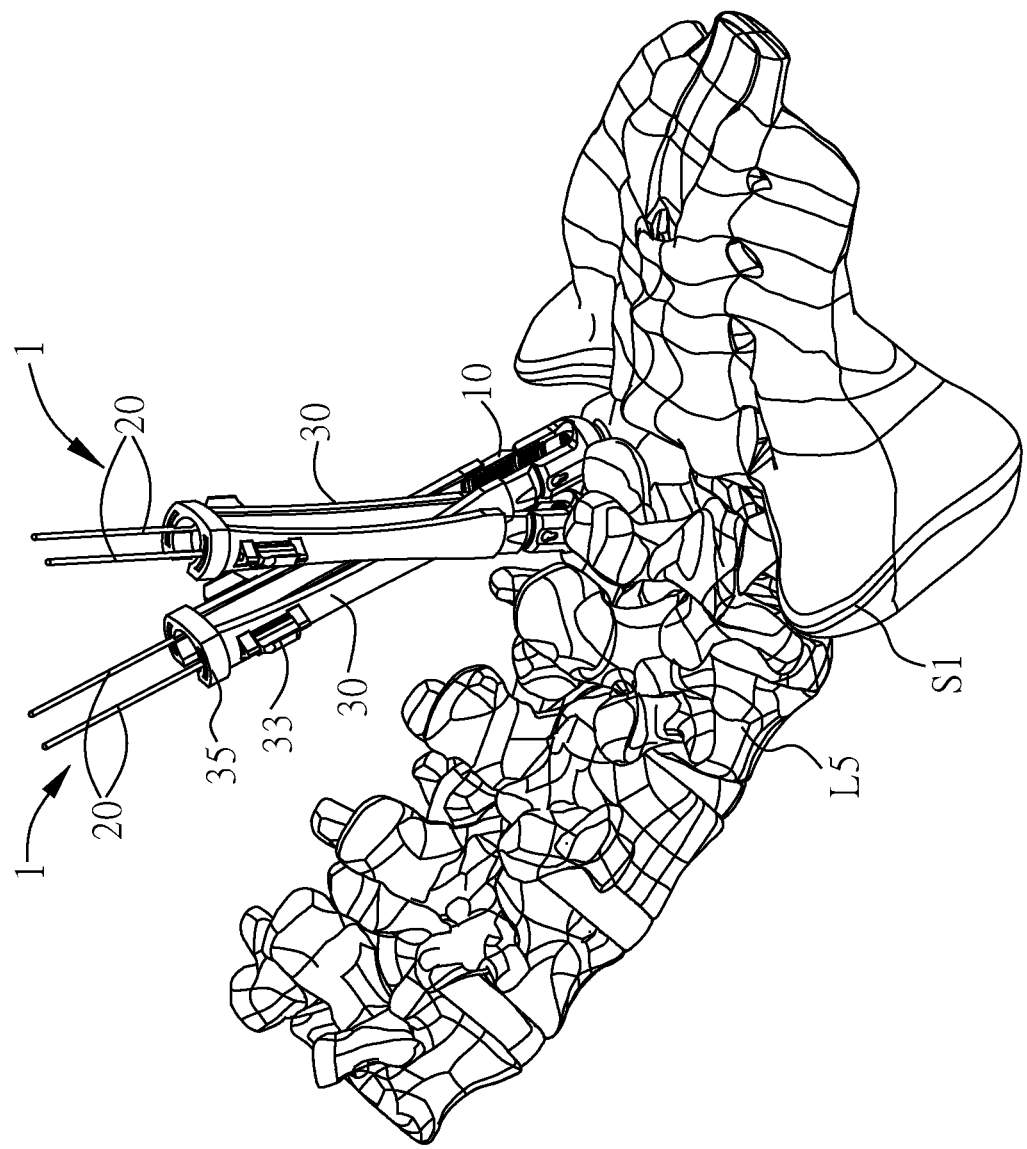
FIG. 8A illustrates a schematic view of the L5 and S1 vertebrae, which are respectively implanted with two devices shown in FIG. 3.
Figure 8B:
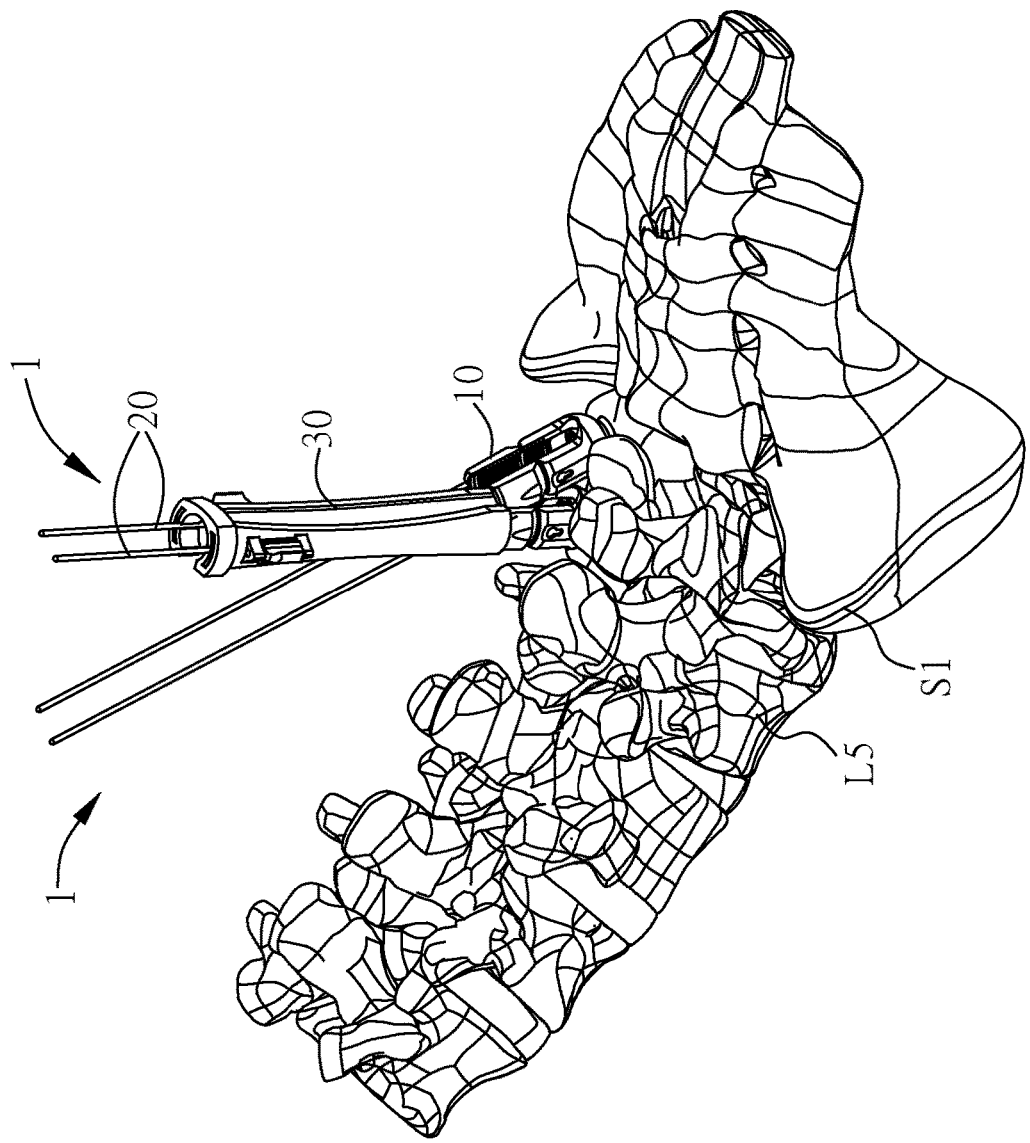
FIG. 8B illustrates a schematic view of removing the extending members on the S1 vertebra shown in FIG. 8A.

Interference may occur between adjacent devices 1, as shown in FIG. 8A, which illustrates a schematic view of the L5-S1 vertebrae respectively implanted with two devices 1 shown in FIG. 3. FIG. 8A shows that in two adjacent devices 1, one of the extending members 30 is forced to pass between two extending members 30 of another device 1. In this case, the surgical instrument cannot approach the screw assembly 10; it is a case of mutual interference. However, this case is rarely seen clinically on the operating table because when the surgeon determines that interference would occur between the extending members 30 based on professional or empirical reasons, the surgeon will try to prevent that interference in advance or adjust the angle of the screw assembly 10 to prevent the case shown in FIG. 8A from occurring. As for other cases of interference, one of the extending members 30 may be excessively tightly attached to the extending member 30 of another device 1, and the two extending members 30 may thus be pulled apart by an external force and then fixed in position such that they do not pass through each other (as shown in FIG. 8A). However, the abovementioned two cases are also considered aspects of interference as referred to herein. If the extending members 30 of the adjacent devices 1 interfere with each other, one or two extending members 30 of one of the devices 1 can be removed, as shown in FIG. 8B, which illustrates a schematic view of removing the extending members on the S1 vertebra shown in FIG. 8A. Although the extending member must be removed, the surgeon only needs to remove the fastener 35 and loosen the supporting member retaining structure 33 (that is, the order is from FIG. 7B to FIG. 7A), and then to remove the extending members 30 straight up along the longitudinal axis Y (shown in FIG. 5B) by separating the supporting members 20 from the through hole 31. It is because that the device 1 of this embodiment still has the supporting members 20 extending through the incision during the surgery, the surgeon can directly align the through holes 31 to the supporting members 20 and lead the supporting members 20 to pass through the through holes 31. After that, the extending members 30 can be easily assembled to the arms 112 of the receiver 11. In the prior art, in which the structure of the extending members 7 or the sleeve 8 used to connect the pedicle screw 9 (9a) is complicated and, in the operation, the connection position is hidden under the skin and muscle tissue. Therefore, once the extending members 7 or sleeve 8 is disassembled, it is difficult to reassemble the extending members 7 or sleeve 8 back to the pedicle screw 9, especially in the case of minimally invasive surgery with a small incision and poor operative field. In addition, the extending members 7 or the sleeve 8 must be pulled outward before separated from the pedicle screw 9 (9a) in the prior art. Obviously, it will require extra operation space, and it may cause the wound to expand or to be pulled. On the other hand, the extending members 30 of this embodiment can be removed straight up along the longitudinal axis Y to avoid a situation in which the wound is enlarged or pulled.

In addition, the present invention further provides an extending assembly for use in a device for stabilization of bone segment. The device includes a screw assembly and two supporting members. The screw assembly includes a receiver, and the receiver has a retainer and two opposite arms, wherein the supporting members are respectively connected to the two arms. As to the detailed structure and connection relationship of the screw assembly and the supporting member, please refer to the screw assembly 10 and the supporting member 20 of the previous embodiment, and no further details are provided herein. Moreover, the extending assembly includes two extending members each having a through hole, and the two supporting members are respectively connected to the two arms through the through holes of the two extending members. As to the two extending members of the extending assembly, it can refer to the extending members 30 of the device 1 of the previous embodiment, and no further details are described herein.

As described above, the present invention provides a device for stabilization of bone and an extending assembly thereof. The device includes a screw assembly and two supporting members, and the supporting members are connected to the two arms of the receiver. The extending assembly has two extending members, each having a through hole. The supporting member passes through the through hole of the extending member, and the bottom end of the extending member is connected to the arm of the receiver. Therefore, the supporting member can be used as the supporting backbone of the extending member to provide a solid foundation that stabilizes the position of the extending member to avoid swinging and displacement, thereby improving the connection stability of the extending member and the arm. During operation, the extending members on both sides will not be skewed or dislodged when subjected to an external force. With this structural design, it can achieve the same stability requirement by using a smaller structure at the connection position of the extending members and the arms; for example, the upper edge of the arm is not required to be additionally thickened for disposing a larger recess, thereby avoiding an increase in the size of the screw and an enlarged surgical wound subsequently.

In addition, in an embodiment of the present invention, the extending member passes through the supporting member to be connected to the arm such that the extending member can be directly removed and reassembled along the fixed direction (for example, the longitudinal axis of the device for stabilization of bone segment). The vertebrae of spinal column from a particular bending angle, especially the five lumbar vertebrae, which form a convex curvature to the abdomen. For example, in the operation, for correcting the L5 and S1 vertebrae, the traditional minimally invasive surgery sometimes encounters the problem of staggering conflicts of extending members. With the implementation of the present invention, if a conflict occurs, one of the extending members can be easily removed along the fixed direction so that the insertion angle of the screw will not be compromised due to the conflict of the extending members. It can also avoid expansion or pulling of the incision during the removal and reassembly (depending on surgery requirements) of the extending members, meanwhile, the supporting member can still temporarily and partially maintain the incision size when the extending member is removed to provide a clear operative field.

The objective, means, and efficiency of the present invention are all different from conventional characteristics in the prior art. It will be appreciated if the committee can review and grant a patent for the benefit of society. However, it should be noted that the described embodiments are only for illustrative and exemplary purposes, and that various changes and modifications may be made to the described embodiments without departing from the scope of the invention as disposed by the appended claims.

What is claimed is:

1. A device for stabilization of a bone segment comprising:
   a screw assembly comprising:
      a receiver having a retainer, a first arm and a second arm, the first arm being opposite the second arm, and the first arm and the second arm extending along a longitudinal axis of the device from positions adjacent to the retainer;
      an anchoring member connected to the retainer;
   a first supporting member connected to the first arm and a second supporting member connected second arm, and the first supporting member and the second supporting member extending along the longitudinal axis respectively;
   a first extending member, having a first through hole and a first recess, wherein the first extending member is sleeved on the first supporting member with the first through hole and moved towards the first arm along the longitudinal axis with the first supporting member as a first axis, and the first extending member is connected to the first arm with the first supporting member passing through the first through hole, and the first recess at an end of the first extending member connected to the first arm, the first recess engages an outside portion of the first arm; and
   a second extending member, having a second through hole and a second recess, the second extending member is sleeved on the second supporting member with the second through hole and moved towards the second arm along the longitudinal axis with the second supporting member as a second axis, and the second extending member is connected to the second arm with the second supporting member passing through the second through hole, and the second recess at an end of the second extending member connected to the second arm, the second recess engages an outside portion of the second arm.

2. The device for stabilization of a bone segment as claimed in claim 1, wherein the first supporting member has a first external thread at one connecting end of first supporting member, and a top surface of the first arm has a first concave portion having a first internal thread corresponding to the first external thread, the first supporting member is screwed and locked to the first arm, and wherein the second supporting member has an second external thread at one connecting end of second supporting member, and a top surface of the second arm has a second concave portion having an second internal thread corresponding to the second external thread, the second supporting member is screwed and locked to the second arm.

3. The device for stabilization of a bone segment as claimed in claim 1, wherein one end of the first through hole is located at a bottom of the first recess; after the first supporting member passes through the first through hole, the first extending member is engaged with the outside portion of the first arm through the first recess to be connected with the first arm; and wherein one end of the second through hole is located at the bottom of the second recess; after the second supporting member passes through the second through hole, the second extending member is engaged with the outside portion of the second arm through the second recess to be connected with the second arm.

4. The device for stabilization of a bone segment as claimed in claim 1, wherein the first recess communicates with an outside of the first extending member through a bottom of the first extending member and a side connected to the bottom thereof, and wherein the second recess communicates with an outside of the second extending member through the bottom of the second extending member and a side connected to the bottom thereof.

5. The device for stabilization of a bone segment as claimed in claim 1, wherein the first extending member has a first supporting member retaining structure disposed thereon to restrict a movement of the first supporting member corresponding to the first extending member; and wherein the second extending member has a second supporting member retaining structure disposed thereon to restrict the movement of the second supporting member corresponding to the second extending member.

6. The device for stabilization of a bone segment as claimed in claim 5, wherein the first extending member has a first retaining hole communicating with the first through hole and an outer space of the first extending member, and the first supporting member retaining structure is disposed adjacent to the first retaining hole and has a first pressing portion for pressing the first supporting member through the first retaining hole; and wherein the second extending member has a second retaining hole communicating with the second through hole and an outer space of the second extending member, and the second supporting member retaining structure is disposed adjacent to the second retaining hole and has an second pressing portion for pressing the second supporting member through the second retaining hole.

7. The device for stabilization of a bone segment as claimed in claim 6, wherein the first supporting member retaining structure is pivotally connected to the first extending member, and the first pressing portion has a first plane; after the first supporting member retaining structure is rotated, the first plane presses the first supporting member; and wherein the second supporting member retaining structure is pivotally connected to the second extending member, and the second pressing portion has a second plane; after the second supporting member retaining structure is rotated, the second plane presses the second supporting member.

8. The device for stabilization of a bone segment as claimed in claim 1, wherein the first arm has a first thickness, the first extending member has a second thickness at a junction formed after the first extending member is connected to the first arm, and a difference between the first thickness and the second thickness is between 0.25 mm and 1 mm.

9. The device for stabilization of a bone segment as claimed in claim 1, wherein the first arm has a first thickness, the first extending member has a second thickness at a junction formed after the first extending member is connected to the first arm, and a difference between the first thickness and the second thickness is substantially equal to the thickness of the first extending member at the end connected to the first arm.

10. The device for stabilization of a bone segment as claimed in claim 1, further comprising a fastener, and the fastener has an engagement slot for engaging with the first and the second extending members at a top end whereof simultaneously.

11. An extending assembly for use in a device for stabilization of a bone segment, wherein the device comprises a screw assembly, a first supporting member and a second supporting member; the screw assembly comprises a receiver having a retainer, a first arm and a second arm, the first arm being opposite the second arm, and the first arm and the second arm extending along a longitudinal axis of the device from positions adjacent to the retainer, the first supporting member is connected to the first arm and the second supporting member is connected second arm, and the first supporting member and the second supporting member extend along the longitudinal axis respectively, the extending assembly comprising:

a first extending member, having a first through hole and a first recess, wherein the first extending member is sleeved on the first supporting member with the through hole and moved towards the first arm along the longitudinal axis with the first supporting member as a first axis, and the first extending member is connected to the first arm with the first supporting member passing through the first through hole, and the first recess at an end of the first extending member connected to the first arm, the first recess engages an outside portion of the first arm; and a second extending member, having a second through hole and a second recess, the second extending member is sleeved on the second supporting member with the second through hole and moved towards the second arm along the longitudinal axis with the second supporting member as a second axis, and the second extending member is connected to the second arm with the second supporting member passing through the second through hole, and the second recess at an end of the second extending member connected to the second arm, the second recess engages an outside portion of the second arm.

12. The extending assembly as claimed in claim 11, wherein one end of the first through hole is located at a bottom of the first recess; after the first supporting member passes through the first through hole, the first extending member is engaged with the outside portion of the first arm through the first recess to be connected with the first arm; and wherein one end of the second through hole is located at the bottom of the second recess; after the second supporting member passes through the second through hole, the second extending member is engaged with the outside portion of the second arm through the second recess to be connected with the second arm.

13. The extending assembly as claimed in claim 11, wherein the first recess communicates with an outside of the first extending member through the bottom of the first extending member and a side connected to the bottom thereof, and wherein the second recess communicates with an outside of the second extending member through the bottom of the second extending member and a side connected to the bottom thereof.

14. The extending assembly as claimed in claim 11, wherein the first extending member has a first supporting member retaining structure disposed thereon to restrict a movement of the first supporting member corresponding to the first extending member; and wherein the second extending member has a second supporting member retaining structure disposed thereon to restrict the movement of the second supporting member corresponding to the second extending member.

15. The extending assembly as claimed in claim 14, wherein the first extending member has a first retaining hole communicating with the first through hole and an outer space of the first extending member, and the first supporting member retaining structure is disposed adjacent to the first retaining hole and has a first pressing portion for pressing the first supporting member through the first retaining hole; and wherein the second extending member has a second retaining hole communicating with the second through hole and an outer space of the second extending member, and the second supporting member retaining structure is disposed adjacent to the second retaining hole and has an second pressing portion for pressing the second supporting member through the second retaining hole.

16. The extending assembly as claimed in claim 15, wherein the first supporting member retaining structure is pivotally connected to the first extending member, and the first pressing portion has a first plane; after the first supporting member retaining structure is rotated, the first plane presses the first supporting member; and wherein the second supporting member retaining structure is pivotally connected to the second extending member, and the second pressing portion has a second plane; after the second supporting member retaining structure is rotated, the second plane presses the second supporting member.

17. The extending assembly as claimed in claim 11, wherein the first arm has a first thickness, the first extending member has a second thickness at a junction formed after the first extending member is connected to the first arm, and a difference between the first thickness and the second thickness is between 0.25 mm and 1 mm.

18. The extending assembly as claimed in claim 11, wherein the first arm has a first thickness, the first extending member has a second thickness at a junction formed after the first extending member is connected to the first arm, and a difference between the first thickness and the second thickness is substantially equal to the thickness of the first extending member at the end connected to the first arm.

* * * * *